United States Patent
Vig et al.

(10) Patent No.: US 6,518,778 B2
(45) Date of Patent: Feb. 11, 2003

(54) METHOD OF DETERMINING ANGLE-OF-CUT

(75) Inventors: John R. Vig, Colts Neck, NJ (US); Arthur Ballato, Oceanport, NJ (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 243 days.

(21) Appl. No.: 09/770,797

(22) Filed: Jan. 23, 2001

(65) Prior Publication Data

US 2002/0097038 A1 Jul. 25, 2002

(51) Int. Cl.$^7$ .................. G01R 29/22; G01R 23/09; H01L 41/08; G01N 23/20

(52) U.S. Cl. ............... 324/727; 324/76.49; 310/360; 378/81

(58) Field of Search ............ 324/76.49, 76.51, 324/727, 725; 310/360, 361, 367; 378/81, 78; 73/702, 54.41

(56) References Cited

U.S. PATENT DOCUMENTS

| 4,412,345 | A | * | 10/1983 | Workman et al. .......... 378/78 |
| 4,499,395 | A | * | 2/1985 | Kahan .................... 310/361 |
| 4,771,446 | A | * | 9/1988 | Howe et al. .............. 378/73 |
| 6,411,676 | B1 | * | 6/2002 | Hooft et al. .............. 378/73 |

OTHER PUBLICATIONS

J.L. Chambers, "An Instrument for Automated Measurement of the Angles of Cut of Doubly Rotated Quartz Crystals," 37th Annual Symposium on Frequency Control, 1983, pp. 275–283.

J.L. Chambers, et al., "An Instrument for Automated Measurement of the Angles of Cut of Doubly Rotated Quartz Crystals", 35th Annual Symposium On Frequency Control, 1981, pp. 60–70.

Knolmayer, E., "X–Ray Goniometry of the Modified Doubly Rotated Cuts", 35th Annual Symposium On Frequency Control, 1981, pp. 56&57.

Kobayashi, Y., "Fully Automated Piezogoniometer (Automatic Quartz Plate Classifier)", 32nd Annual Symposium on Frequency Control, 1978, pp. 310–316.

(List continued on next page.)

Primary Examiner—N. Le
Assistant Examiner—James Kerveros
(74) Attorney, Agent, or Firm—Michael Zelenka; George B. Tereschuk

(57) ABSTRACT

Methods are included for determining deviations from $\phi=0°$ in test resonators based on the quasi-pure modes' displacement ratio variations with $\phi$ angle. A direct relationship between deviation from $\phi=0°$ and the c-mode displacement ratio has been observed, so that the larger the deviation from $\phi=0°$, then the larger is the change in the normalized frequency of the c-mode upon immersion in, or contact with, a fluid. The method includes measuring $\theta$ and $\phi$ angles in reference resonators with different small $\phi$ angles and quasi-pure mode frequencies of reference resonators in both air and a test fluid at ambient temperatures, calculating the normalized frequency changes between the air and fluid measurements as a reference point, measuring the test resonator in air then in the fluid and comparing the results. Also includes are similar methods for measuring the $\phi$ angles in the quasi-pure mode of near-BT-cut resonator plates and the LGX family of rotated-y-cut ZTC crystal resonators, so that the appropriate modes' displacement ratio variations with the $\phi$ angle determine deviations from $\phi=0°$. In the preferred method of this invention the test fluid used for measuring a reference fluid quasi-pure mode frequency is pure water at ambient temperature.

105 Claims, 3 Drawing Sheets

OTHER PUBLICATIONS

J. Clastre, et al., "Goniometric Measurements of the Angles of Cut of Doubly Rotated Quartz Plates", 32nd Annual Symposium on Frequency Control, 1978, pp. 310–316.

J.F. Darces, et al., "Final Z–Ray Control of the Orientation of Round or Rectangular Quartz Slides for Industrial Purposes", 32nd Annual Symposium on Frequency Control, 1978, pp. 304–309.

V.E. Bottom, *Introduction to Quartz Crystal Unit Design*, Van Nostrand Reinhold Company, Chapter 10, 1982.

J.A. Kusters, "Resonator and Device Technology", in E.A. Gerber and A. Ballato; *Precision Frequency Control*, vol. 1, pp. 161–171, Academic Press, 1985.

C.A. Adams et al., "X–Ray Technology—A Review", Proc. 41st Annual Cymposium on Frequency Control, 1987, pp. 249–257; and.

H. Bradaczek, Automated X–Ray Sorting Machine for Round Quartz Blanks, 45th Annual Symposium on Frequency Control, 1991, pp. 114–116.

* cited by examiner

METHOD OF DETERMINING ANGLE-OF-CUT

GOVERNMENT INTEREST

The invention described herein may be manufactured, used, imported, sold, and licensed by or for the Government of the United States of America without the payment to us of any royalty thereon.

FIELD OF THE INVENTION

This invention relates in general to the field of crystal resonators, and more particularly to methods of determining the angles-of-cut of doubly rotated crystal resonators.

BACKGROUND OF THE INVENTION

The frequency vs. temperature ("f vs. T") characteristics of crystal resonators depend on the angles of cut of the quartz plate with respect to the crystallographic axes. In certain applications, an accuracy within seconds of arc is required. Due to imperfections in both the cutting techniques and the quartz, the angles of cut of each blank must be measured, the blanks must be sorted, and, if necessary, angle-corrected to achieve the required angles-of-cut precision.

X-ray diffraction is the standard technique for measuring angles-of-cut, and double-crystal X-ray diffraction is generally used to measure the angles between the major surface of a blank and a specified set of atomic planes. In this technique, X-rays are reflected from atomic planes in a crystal in accordance with Bragg's law: $n\lambda=2d \sin \theta_B$, where $\lambda$ is the wavelength of the reflected X-rays and $\theta_B$=the "Bragg angle," the angle at which the peak of the reflection occurs. References on the X-ray techniques are J. L. Chambers, "An Instrument for Automated Measurement of the Angles of Cut of Doubly Rotated Quartz Crystals," 37th Annual Symposium on Frequency Control, 1983, pp 275–283 and J. L. Chambers, et al., "An Instrument for Automated Measurement of the Angles of Cut of Doubly Rotated Quartz Crystals," 35th Annual Symposium On FrequencyControl, 1981, pp. 60–70. In most X-ray orientation systems, the $K_\alpha$ radiation from a copper target is used because the wavelength of this radiation is near the typical atomic spacings.

Referring now to FIG. 1, which illustrates double-crystal X-ray diffraction, the monochromator crystal collimates the X-rays, allowing more accurate determination of the Bragg angle than is possible with single-crystal orientation systems. The goniometer allows varying the angle of incidence of the X-rays and determining the angle of maximum reflection. When a laser is used to define the plane of the blank, a measurement precision of ~2 seconds of arc is possible. Also, the X-ray and goniometer techniques can be combined in an X-ray goniometer as described in Knolmayer "X-Ray Goniometer of the Modified Doubly Rotated Cuts," 35th Annual Symposium On Frequency Control, 1981, pp. 567. Other priors art techniques are based on an automated piezogonimeter described in Kobayashi, "Fully Automated Piezogoniometer (Automatic Quartz Plate Classifier)," 32nd Annual Symposium on Frequency Control, 1978: p 317–320.

The AT angle-of-cut presents a different problem not addressed by prior art techniques. The AT-cut is the most commonly used zero temperature coefficient ("ZTC") thickness shear mode resonator. The AT-cut's angles of cut are about $\theta=35°15'\pm30'$ and $\phi=0°$, as depicted in FIG. 2. The $\theta$ angle is the primary determinant of the resonator's f vs. T characteristic. Therefore, it is intentionally adjusted to a precise value typically within the ±30' range, depending on the application. The $\phi$ angle is usually not measured during manufacturing operations for two reasons. First, a small error in the $\phi$ angle generally has only small effects on the f vs. T characteristic of the resonator. Secondly, the equipment needed to measure both $\theta$ and $\phi$ angles is quite expensive, with an average cost exceeding $100,000 per instrument. The prior art X-ray diffraction and goniometer methods are particularly unsuitable for measuring errors in the $\phi$ angle, because their errors are not always small, and even small $\phi$ angle errors are not negligible for certain applications. For example, errors in the $\phi$ angle can result in significant manufacturing yield problems. Such errors also effect properties such as the AT-cut's sensitivity to electric fields, i.e., when $\phi=0°$, the AT-cut is insensitive to electric fields, but when $\phi\neq 0°$, the AT-cut exhibits a finite sensitivity to electric fields. Prior art techniques are generally not satisfactory and are costly. There are no known inexpensive techniques for measuring the deviations from $\phi=0°$. Thus, there has been a long-felt need to determine inexpensively whether the $\phi$ angle deviates from $\phi=0°$.

The inventors have observed that the effects of c-modes' displacement ratio i.e. the ratio of out-of-plane to in-plane displacement, variations with $\phi$ angle can be used to determine deviations from $\phi=0°$. They have observed a direct relationship between deviation from $\phi=0°$ and the c-mode displacement ratio, so that the larger the deviation from $\phi=0°$, then the larger is the change in the normalized frequency of the c-mode upon immersion in, or contact with, a fluid. Thus, $\phi$ angle deviations are determined by measuring $\theta$ and $\phi$ angles of standard resonators with different small $\phi$ angles, i.e. less than or equal to 7°, and their quasi-pure mode frequencies in ambient air and a test fluid, calculating the normalized frequency changes between the air and fluid measurements, measuring the test resonator in air and then in fluid, and then comparing the results. Accordingly, this invention fulfills the long-felt need to determine inexpensively $\phi$ angle deviation by providing methods of determining the $\phi$ angle-of-cut, which do not suffer from the disadvantages, shortcomings and limitations of the current expensive, time-consuming and cumbersome testing equipment. Other useful prior art references are:

J. Clastre et al. "Goniometric Measurements of the Angles of Cut of Doubly Rotated Quartz Plates," Proc. 32 th Ann. Symposium on Frequency Control, pp. 310–316, 1978;

J. F. Darces et al., "Final X-Ray Control of the Orientation of Round or Rectangular Quartz Slides for Industrial Purposes," Proc. 32 th Ann. Symposium on Frequency Control, pp. 304–309, 1978;

V. E. Bottom, *Introduction to Quartz Crystal Unit Design*, Van Nostrand Reinhold Company, Chapter 11, 1982;.

J. A. Kusters, "Resonator and Device Technology," in E. A. Gerber and A. Ballato; *Precision Frequency Control*, Vol. 1, pp.161–183, Academic Press, 1985;

C. A. Adams et al., "X-Ray Technology—A Review," Proc. 41 st Ann. Symposium on Frequency Control, pp. 249–257, 1987; and H. Bradaczek, "Automated X-Ray Sorting Machine For Round Quartz Blanks," Proc. 45 th Ann. Symposium on Frequency Control, pp. 114–116, 1991.

SUMMARY OF THE INVENTION

It is therefore one object of the present invention to provide methods and techniques to determine whether the $\phi$ angle deviates from φ=0° based on the quasi-pure modes' displacement ratio variations with the φ angle.

It is another object of the present invention to provide methods and techniques to determine whether the φ angle deviates from φ=0° based on the c-modes' displacement ratio variations with the φ angle.

It is still another object of this invention to provide methods and techniques to determine whether the φ angle in a near AT angle-of-cut deviates from φ=0° based on the c-modes' displacement ratio variations with the φ angle.

It is yet another object of this invention to provide methods and techniques to determine whether the φ angle in a near BT angle-of-cut deviates from φ=0° based on the b-modes' displacement ratio variations with the φ angle.

It is still a further object of this invention to provide methods and techniques to determine whether the φ angle in the LGX family of rotated-y-cut ZTC crystal resonators deviates from φ=0° based on the quasi-shear modes' displacement ratio variations with the φ angle. The term "LGX" is well-known to those skilled in the art as a shorthand expression for a family of piezoelectric crystals, including the langasite (LGS), langanite (LGN), langatate (LGT) and so on.

To attain these and other objects and advantages, the present invention provides methods for determining deviations from φ=0° in test resonators based on the quasi-pure modes' displacement ratio variations with φ angle. The method comprises measuring θ and φ angles in reference resonators with different small φ angles and quasi-pure mode frequencies of reference resonators in both ambient air and a test fluid, calculating the normalized frequency changes between the air and fluid measurements as a reference point, measuring the test resonator in air then in fluid and comparing the results. Also contemplated are similar methods for measuring the φ angles in the quasi-pure mode of near-BT-cut resonator plates and the LGX family of rotated-y-cut ZTC crystal resonators, so that the appropriate modes' displacement ratio variations with the φ angle determine deviations from φ=0°. It is well-known in the resonator art that the designations "c" and "b" modes simply refer to the uncoupled, or pure, mode that exists in rotated Y cuts of crystals having group point symmetry 32. Departure from the φ=0° condition introduces a slight coupling of the modes, so that the pure mode becomes "quasi-pure, with an admixture of out-of-plane motions that increase with the increasing φ value. The methods of this invention are based on the principle that the larger the deviation from φ=0°, the larger is the change in the normalized frequency of the quasi-pure mode upon immersion into a fluid. In the preferred embodiment of the methods of this invention the test fluid used for measuring a reference fluid quasi-pure mode frequency is pure water at ambient temperature. Temperature can affect the results, so preferably, the measurements on the reference resonators and test resonators are made at the same temperature. If the measurements are not made at the same temperature, then errors on the order of 1 ppm per degree C. can result. This compares with the normalized frequency changes on the order of a 100 ppm per degree change in Q-angle. For known θ angles, it is possible to compensate for the effects of temperature.

The exact nature of this invention, as well as other objects and advantages thereof, will be readily apparent from consideration of the following specification relating to the annexed drawings.

DETAILED DESCRIPTION OF METHODS

Figure 1:
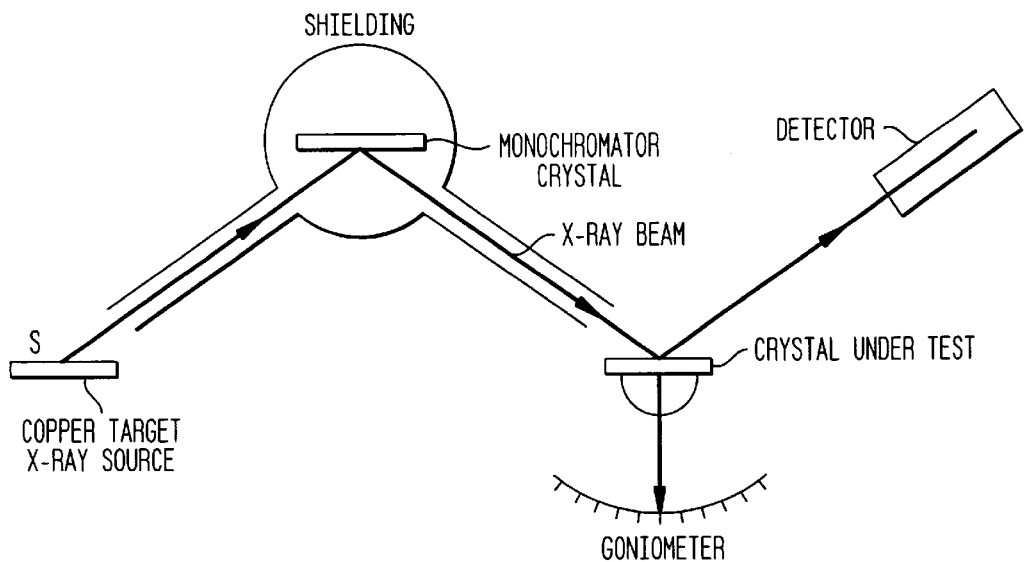
FIG. 1 illustrates a prior art double-crystal X-ray diffraction system.
Figure 2:
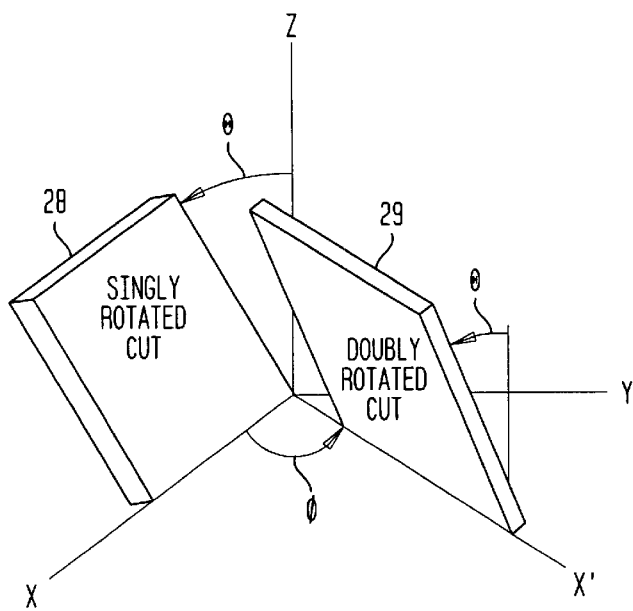
FIG. 2 is a schematic pictorial view showing slicing planes for singly rotated and doubly rotated cuts with respect to the conventional orthogonal crystallographic X-Y-Z axes, and rotation angles θ and φ.

An understanding of the c-mode and φ angle in AT-cut resonators is useful before describing the methods of the present invention. Referring now to the drawings, FIG. 2 shows conventional X-Y-Z crystallographic axes with slicing planes 28 and 29 located thereon. Plane 28 represents a plane along which a singly rotated cut would be made in a crystal with respect to its X-Y-Z axes. Plane 29 illustrates the plane along which a doubly rotated cut would be made. A doubly rotated cut is made along a plane that forms angle θ with respect to the Z-axis, and includes axis X' that lies in the X-Y plane and forms angle φ of interest with the X-axis.

Figure 3:
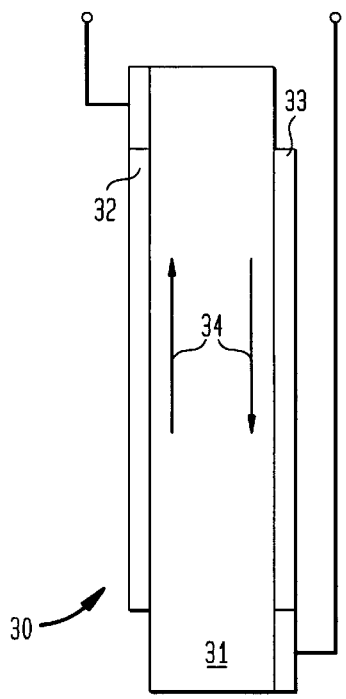
FIGS. 3 and 4 are side elevations, showing an edge of a singly rotated resonator.
Figure 4:
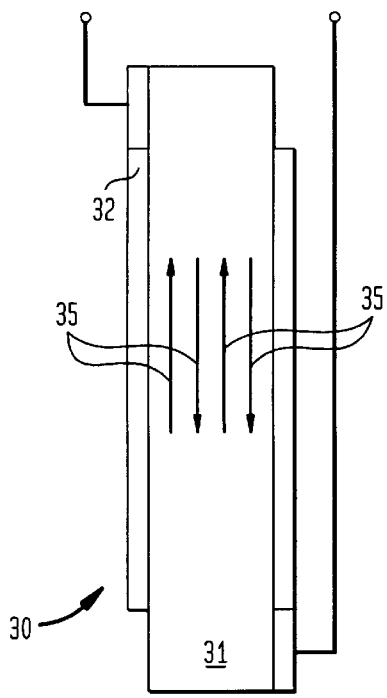

FIGS. 3 and 4 illustrate the fundamental and third overtone c-modes, respectively, by showing an edge of singly rotated resonator 30 having piezoelectric plate 31 sliced from a bulk crystal (not shown) along FIG. 2's plane 28. Resonator 30 represents a standard circular, AT-cut quartz resonator, with metallic electrodes 32 and 33 deposited on opposite major surfaces of plate 31. FIG. 3 arrows 34 depict the directions of mechanical vibration, at a single instant of time, that plate 31 performs in response to the application of a drive voltage across electrodes 32 and 33. In particular, arrows 34 represent operation at a fundamental, thickness-shear mode (TSM), that is, a fundamental c-mode. Resonator 30 may also be driven at other overtones of the c mode, such as arrows 35 in FIG. 4, which illustrate the vibration directions for resonator 30 when driven at a third-overtone c-mode. As indicated with arrows 34 and 35 in FIGS. 3 and 4, the vibrations at the major surfaces of resonator 30 are directed parallel to the planar, major surfaces of resonator 30.

As indicated above, the c-mode of a singly rotated, temperature-compensated crystal, such as an AT-cut crystal, is a pure TSM, characterized by surface displacements in the plane of the plate only. The modal displacements of doubly rotated crystals, on the other hand, have components that are out of the plane of the crystal plate. When a doubly rotated resonator, e.g., when θ≈35°, and 0°>φ≧30°, is operated, the displacements at the surface are not entirely in the plane of the plate. On a temperature-compensated locus of cuts, for example, as angle φ increases, the out-of-plane displacements of the c-modes of vibration also increase. The out-of-plane displacements of the b-mode and a-mode of vibration also change with angle φ.

Figure 5:
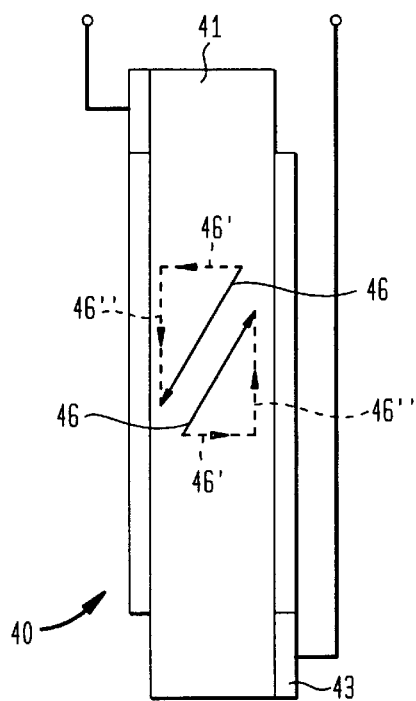
FIGS. 5 and 6 are side elevations, similar to FIGS. 4 and 5, respectively, showing an edge of a doubly rotated resonator.
Figure 6:
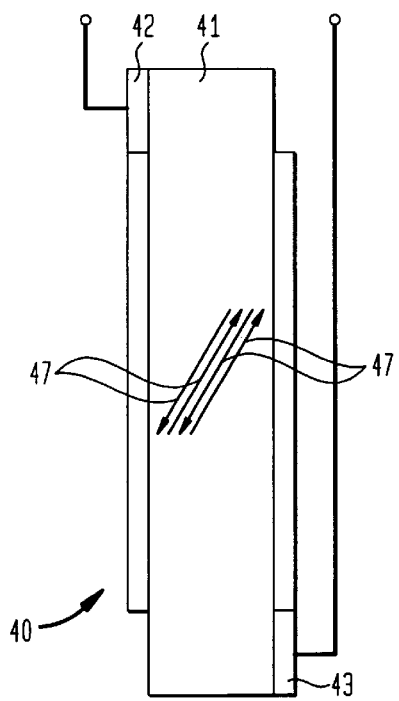

FIGS. 5 and 6 show an edge of doubly rotated resonator 40 having piezoelectric plate 41 sliced from a bulk crystal (not shown) along plane 29 of FIG. 2. Metallic electrodes 42 and 43 are deposited on opposite faces of plate 41, and oblique arrows 46 in FIG. 5 depict the directions of mechanical vibration that plate 41 exhibits in response to the application of an appropriate drive voltage across electrodes 42 and 43. Arrows 46 represent the displacements obtained when resonator 40 is excited on a slow, quasi-shear mode, commonly referred to as the c-mode. Drive voltages may simultaneously excite resonator 40 on a fast, quasi-shear mode, called the b-mode, and/or on a quasi-longitudinal mode, called the a-mode. Moreover, doubly rotated resonator 40 can also be excited on various overtones of each of these modes, e.g., on the fundamental, third overtone and fifth overtone. Arrows 47 in FIG. 6 illustrate displacements for a third-overtone c-mode of doubly rotated resonator 40.

Arrows 46 and 47 represent the oblique displacements of interest that are resolvable into in-plane and out-of-plane components. For example, FIG. 5 shows arrow 46 resolved into in-plane component 46" and out-of-plane component 46'. Arrows 47 may be resolved into similar components. The displacements associated with out-of-plane component 46' propagate a damped compressional wave into an adjacent liquid. The displacements of in-plane component 46" propagate a damped shear wave in the liquid. Additionally, with changing values of angle $\phi$, out-of-plane components 46' of the various modes change, and so do the effects of the liquid on the frequencies (and Q's) of the various modes of vibration. Thus, the interaction at a resonator-fluid interface by varying angle $\phi$ can be precisely controlled in a resonator. Moreover, because these different modes of vibration at the different $\phi$ angles generally react differently with a fluid, each mode of vibration and $\phi$ angle will result in a different frequency change.

Since different vibration modes at different $\phi$ angles generally react differently with a fluid, so that each mode of vibration and $\phi$ angle will result in a different frequency change, errors in $\phi$ angle can be determined by measuring frequency changes. Therefore, one inexpensive method for determining the error in $\phi$ angle is as follows. Measure $\theta$ and $\phi$ angles of a group of reference resonators of different small $\phi$ angles whose angles-of-cut have been carefully measured with a precision x-ray diffraction instrument. A small $\phi$ angle-of-cut is considered less than or equal to 7°. Measure the reference frequencies of a quasi-pure mode of the different $\phi$ angle reference resonators in room temperature air and again in a room temperature test fluid, such as pure water. Calculate the normalized frequency changes between the air and fluid measurements, and use this data as the reference to which the results from resonators of unknown $\phi$ angles are compared. To determine the $\phi$ angle of a near-AT-cut resonator of unknown $\phi$ angle, measure the resonator in air then in distilled water, and then compare the results with calibration data obtained from measuring the normalized frequency changes of the reference resonators. Inasmuch as the resonator's surface roughness and contours also effect the normalized frequency changes, for best results, the reference resonators should possess the same surface roughness and contour as the unknown resonator.

Because normalized frequency changes are used, the results are independent of the absolute frequencies of the resonators. For example, if calibration data are taken using reference resonators of 10 MHz nominal frequency, the data apply to test resonators of any frequency as long as the comparison is made with normalized ($\Delta f/f$) readings.

Figure 7:
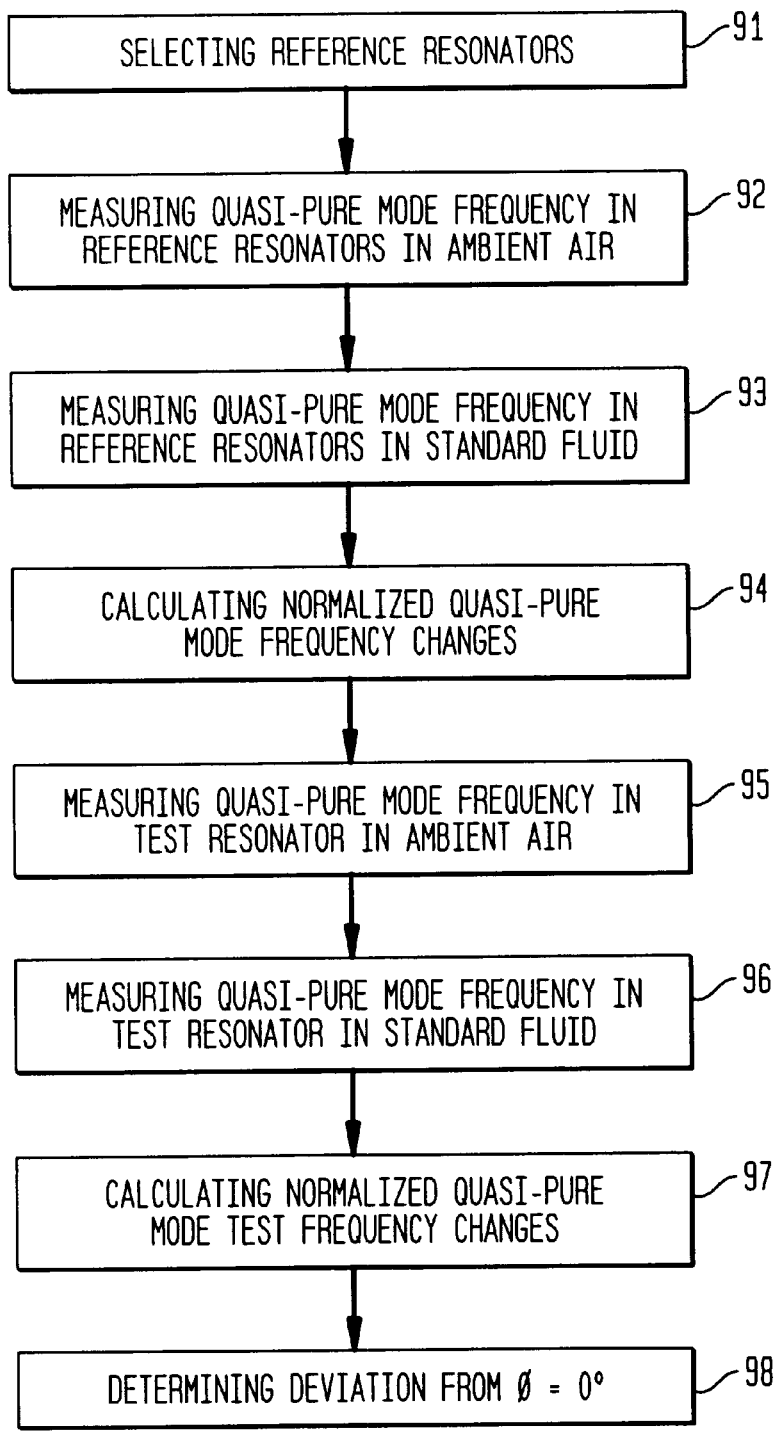
FIG. 7 is a block diagram illustrating the steps of determining the φ angle in quasi-pure mode frequencies used in all methods of the present invention.

Before referring to FIG. 7, it is important to define the terms pure mode and quasi-pure mode. A pure mode is a mode that has particle motion purely in the plane of the plate, or normal to the plane of the plate. By contrast, the quasi-pure mode is substantially pure yet nonetheless has some component of displacement that is neither in the plate nor normal to it. The singly rotated cut, such as AT and BT are pure modes, and doubly rotated cuts, in general, are quasi-pure modes.

Referring now to the drawings, FIG. 7 illustrates the steps of the method of the present invention for determining error in an $\phi$ angle of quasi-pure mode frequencies, including the AT-cut, BT-cut and the LGX family of rotated-y-cut ZTC test resonators. This method commences with a selecting step 91 including providing a first group of reference resonators, each having a $\theta$ angle-of-cut and a $\phi$ angle-of-cut, measuring the $\theta$ and $\phi$ angles-of-cut and then selecting a plurality of reference resonators having small $\phi$ angles-of-cut, which are defined as less than or equal to 7°. For example, the plurality of resonators could have selected Q values of 0.1°, 0.2°, 0.3°, 0.5°, 1.0°, 2.0°, 4.0° and 7.0°. It is preferred that this step be performed with an x-ray diffraction means. In a reference air-measuring step 92, the second plurality of reference resonators is excited in ambient air at different frequencies, including the quasi-pure mode frequency, and the quasi-pure mode frequency of each resonator in air is measured. In a reference fluid-measuring step 93, the second plurality of reference resonators is excited in a test fluid, such as water or pure water at ambient temperature, at different frequencies, including the quasi-pure mode frequency, and the quasi-pure mode frequency of the resonators in the fluid is measured. In a reference-calculating step 94, the normalized frequency changes between the reference air quasi-pure mode frequencies and the reference fluid quasi-pure mode frequency are calculated. Completing these steps results in establishing the necessary reference parameters.

The method for determining $\phi$ angle error continues with a test air-measuring step 95 comprising measuring in air a quasi-pure mode frequency of the test resonator after exciting the test resonator at the quasi-pure mode frequency. For fluid-measuring step 96, the test resonator is excited in the test fluid at the quasi-pure mode frequency and the quasi-pure mode frequency in the test resonator is measured. During a calculating step 97, the normalized test frequency changes between the quasi-pure mode frequencies in air and the quasi-pure mode frequencies in fluid are calculated to determine the test resonator's Q-angle. It should be noted that the FIG. 7 steps illustrate the steps of determining the $\phi$ angle in quasi-pure mode frequencies, and that the steps are also employed for other modes, frequencies and angles of other methods of the present invention.

In one experiment in accordance with the present invention's method, when a $\phi=0°$ and a $\phi=2°$ resonator were measured in air and then in water, the $\phi=2°$ resonator's air-to-water frequency change was about 200 parts per million larger than the $\phi=0°$ resonator's air-to-water frequency change.

When this method is employed for determining the $\phi$ angle in an AT-cut resonator, the c-mode frequency is measured and calculated, and the c-mode's frequency change variations with $\phi$ angle can be used for determining deviations from $\phi=0°$. A similar method can be applied to measuring the $\phi$ angles of near-BT-cut resonator plates, except that the b-mode of the near-BT-cuts is to be used, i.e., the b-mode's displacement ratio variations with $\phi$ angle result in frequency changes that can be used for determining deviations from $\phi=0°$. The larger the deviation from $\phi=0°$, the larger is the change in the normalized frequency of the b-mode upon immersion into a fluid. It is also within the contemplation of this invention, to employ these methods for other materials in the same crystal class as quartz with one or more rotated-y-cut ZTC's based on the quasi-shear mode frequency.

It is also within the contemplation of this invention to avoid plating electrodes onto the crystals and to avoid making measurements while the blanks are immersed in a liquid. In a preferred embodiment of the methods of the present invention one may simply excite via an air gap, or by lateral field excitation applied from beneath, or from above, the blanks and then just touch the bottom side of the blanks to the surface of the standard fluid, e.g. a beaker of water. In this method, the blanks could be held in place by suction. Then, apply to the upper surface of each blank, in a controlled manner, a uniformly sized drop of water. By making the surface hydrophilic immediately before the drop is applied, e.g. by UV-ozone cleaning, or a surfactant, then the low contact angle so created will make the drop spread from edge to edge, thereby resulting in a thin, uniform layer of water which affects the frequency in a more predictable way than a bead of water. Thus, the fluid testing step 93 can also be varied by applying a fluid instead of measuring the quasi-pure mode frequency in reference resonators in a standard fluid.

Another variation of the present method is to augment the fluid testing steps 93 and 96 by adding air or other inexpensive clean gases such as nitrogen at different pressure values. For example, multiple resonators in a chamber could be tested for frequency at one time. Then the chamber pressure could be increased and the set of frequency measurements for the group of resonators could all be tested for frequency at once. This can be followed by increasing chamber pressure further, repeating the frequency measurements and so on. Based on such an ensemble of frequency readings for each resonator as a function of gas pressure, the $\phi$ values of all resonators in the test set can be obtained by comparison with similar pressure readings taken on the reference set having known $\phi$ values. It is also possible to replace the fluid testing steps 93 and 96 by adding air or other inexpensive clean gases such as nitrogen at different pressure values instead of a fluid.

A number of variations of the methods of the present invention are possible and they are all considered to be within the scope of this invention. Thus many other applications, modifications and variations of the present invention will become evident to those skilled in these arts in the light of the above teachings. Similarly, the principles of the present invention may apply to other types of crystals and any other modes in which a compressional wave is inadvertently generated. It is to be understood, therefore, that within the scope of the appended claims, the invention may be practiced otherwise than as specifically described.

What we claim is:

1. A method for determining error in a $\phi$ angle of a test resonator, comprising the steps of:

selecting a plurality of reference resonators having small $\phi$ angles-of-cut;

measuring a reference frequency of a quasi-pure mode in each of said plurality of reference resonators excited in ambient air;

measuring a reference frequency of the quasi-pure mode in each of said plurality of reference resonators excited in a test fluid;

calculating a normalized quasi-pure mode frequency change between said reference air frequency and said reference fluid frequency for each of the plurality of reference resonators;

measuring a test frequency of the quasi-pure mode in the test resonator excited in said ambient air, said test resonator having an unknown $\phi$ angle-of-cut;

measuring a frequency of the quasi-pure mode of the test resonator excited in said test fluid at said quasi-pure mode frequency;

calculating a normalized test quasi-pure mode frequency change between said test air frequency and said test fluid frequency to determine a quasi-pure mode displacement ratio for said test resonator; and determining a deviation amount from said unknown $\phi$ angle-of-cut and 0°.

2. The method for determining $\phi$ angle error of the test resonator, as recited in claim 1, wherein said small $\phi$ angles-of-cut are less than or equal to 7°.

3. The method for determining $\phi$ angle error of the test resonator, as recited in claim 2, wherein said test fluid is water.

4. The method for determining $\phi$ angle error of the test resonator, as recited in claim 3, wherein said test fluid is pure water at an ambient temperature.

5. The method for determining $\phi$ angle error of the test resonator, as recited in claim 4, further comprising the step of selecting said plurality of reference resonators with a surface roughness similar to said test resonator.

6. The method for determining $\phi$ angle error of the test resonator, as recited in claim 5, further comprising the step of selecting said plurality of reference resonators with a surface contour similar to said test resonator.

7. The method for determining $\phi$ angle error of the test resonator, as recited in claim 6, further comprising measuring an $\theta$ angle-of-cut in a first group of reference resonators before said selecting step.

8. The method for determining $\phi$ angle error of the test resonator, as recited in claim 7, further comprising the step of comparing a reference air frequency measurement with a test air frequency measurement during said calculating step.

9. The method for determining $\phi$ angle error of the test resonator, as recited in claim 8, further comprising the step of comparing a reference water frequency measurement with a water frequency measurement during said calculating step.

10. The method for determining $\phi$ angle error of the test resonator, as recited in claim 9, further comprising said test resonator having an AT angle-of-cut.

11. The method for determining $\phi$ angle error of the test resonator, as recited in claim 10, further comprising said quasi-pure mode frequency being a c-mode frequency.

12. The method for determining $\phi$ angle error of the test resonator, as recited in claim 9, further comprising said test resonator having a BT angle-of-cut.

13. The method for determining $\phi$ angle error of the test resonator, as recited in claim 12, further comprising said quasi-pure mode frequency being a b-mode frequency.

14. The method for determining $\phi$ angle error of the test resonator, as recited in claim 9, further comprising said test resonator having a rotated-y-cut ZTC angle-of-cut.

15. The method for determining $\phi$ angle error of the test resonator, as recited in claim 14, further comprising said quasi-pure mode frequency being a quasi-shear mode frequency.

16. The method for determining $\phi$ angle error of the test resonator, as recited in claim 9, further comprising each of said first group of reference resonators having said $\theta$ angle-of-cut.

17. The method for determining $\phi$ angle error of the test resonator, as recited in claim 16, further comprising measuring said $\theta$ angle-of-cut and said $\phi$ angle-of-cut with an x-ray diffraction means.

18. The method for determining $\phi$ angle error of the test resonator, as recited in claim 17, further comprising the step of exciting said plurality of reference resonators in said ambient air at a plurality of different frequencies during the measuring reference air frequency step.

19. The method for determining $\phi$ angle error of the test resonator, as recited in claim 18, further comprising the step of exciting said quasi-pure mode frequency during the measuring reference air frequency step.

20. The method for determining φ angle error of the test resonator, as recited in claim 19, further comprising the step of exciting said plurality of reference resonators in said ambient pure water at a plurality of different frequencies during said measuring reference fluid frequency step.

21. The method for determining φ angle error of the test resonator, as recited in claim 20, further comprising the step of exciting said quasi-pure mode frequency during the measuring reference fluid frequency step.

22. The method for determining φ angle error of the test resonator, as recited in claim 21, further comprising the steps of:
    exciting an unplated blank of said test resonator by lateral field excitation from beneath said unplated blank; and
    applying a uniformly sized drop of water to an upper surface of said unplated blank.

23. The method for determining φ angle error of the test resonator, as recited in claim 22, further comprising the step of UV-ozone cleaning said unplated blank before said water applying step to result in a low contact angle created by the UV-ozone.

24. The method for determining φ angle error of the test resonator, as recited in claim 23, wherein said UV-ozone cleaning step causes said drop of water to spread from edge to edge of the unplated blank resulting in a thin, uniform layer of water affecting the quasi-pure mode frequency.

25. The method for determining φ angle error of the test resonator, as recited in claim 2, wherein said test fluid is a gas.

26. The method for determining φ angle error of the test resonator, as recited in claim 25, further comprising the step of applying a plurality of pressure values to said gas.

27. The method for determining φ angle error of the test resonator, as recited in claim 26, further comprising the step of testing a group of test resonators in a test chamber for a given frequency at one time.

28. The method for determining φ angle error of the test resonator, as recited in claim 27, further comprising the steps of:
    increasing a test chamber pressure value during the group testing step; and
    testing a multiple set of frequency measurements for said group all at once.

29. The method for determining φ angle error of the test resonator, as recited in claim 28, further comprising the step of repeating said frequency measurement steps.

30. The method for determining φ angle error of the test resonator, as recited in claim 29 further comprising the steps of:
    obtaining a plurality of reference gas pressure readings from said reference set of test resonators having known φ values; and
    comparing a plurality of frequency readings for each of said group of test resonators as a function of gas pressure with said plurality of gas reference pressure readings.

31. The method for determining φ angle error of the test resonator, as recited in claim 30, wherein said gas is nitrogen.

32. A method for determining error in a φ angle of an AT angle-of-cut test resonator, comprising the steps of:
    selecting a plurality of reference resonators having small φ angles-of-cut;
    measuring a reference frequency of a c-mode in each of said plurality of reference resonators excited in ambient air;
    measuring a reference frequency of the c-mode in each of said plurality of reference resonators excited in a test fluid;
    calculating a plurality of normalized c-mode frequency changes between said reference air frequency and said reference fluid frequency;
    measuring a frequency of the c-mode in the test resonator excited in said ambient air, said test resonator having an unknown φ angle-of-cut;
    measuring a frequency of the c-mode of the test resonator excited in said test fluid at said c-mode frequency;
    calculating a normalized test c-mode frequency change between said test air frequency and said test fluid frequency to determine a c-mode displacement ratio for said test resonator; and
    determining a deviation amount from said unknown φ angle-of-cut and 0°.

33. The method for determining φ angle error of the AT angle-of-cut test resonator, as recited in claim 32, wherein said small φ angles-of-cut are less than or equal to 7°.

34. The method for determining φ angle error of the AT angle-of-cut test resonator, as recited in claim 33, wherein said test fluid is water.

35. The method for determining φ angle error of the AT angle-of-cut test resonator, as recited in claim 34, wherein said test fluid is ambient pure water.

36. The method for determining φ angle error of the AT angle-of-cut test resonator, as recited in claim 35, further comprising the step of selecting said plurality of reference resonators with a surface roughness similar to said test resonator.

37. The method for determining φ angle error of the AT angle-of-cut test resonator, as recited in claim 36, further comprising the step of selecting said plurality of reference resonators with a surface contour similar to said test resonator.

38. The method for determining φ angle error of the AT angle-of-cut test resonator, as recited in claim 37, further comprising measuring an θ angle-of-cut in a first group of reference resonators before said selecting step.

39. The method for determining φ angle error of the AT angle-of-cut test resonator, as recited in claim 38, further comprising the step of comparing a reference air frequency measurement with a test air frequency measurement during said calculating step.

40. The method for determining φ angle error of the AT angle-of-cut test resonator, as recited in claim 39, further comprising the step of comparing a reference water frequency measurement with a water frequency measurement during said calculating step.

41. The method for determining φ angle error of the AT angle-of-cut test resonator, as recited in claim 40, further comprising measuring said θ angle-of-cut and said φ angle-of-cut with an x-ray diffraction means.

42. The method for determining φ angle error of the AT angle-of-cut test resonator, as recited in claim 41, further comprising the steps of:
    exciting an unplated blank of said test resonator by lateral field excitation from beneath said unplated blank;
    UV-ozone cleaning said unplated blank to result in a low contact angle created by the UV-ozone;
    applying a uniformly sized drop of water to an upper surface of said unplated blank; and
    said UV-ozone cleaning step causes said drop of water to spread from edge to edge of the unplated blank resulting in a thin, uniform layer of water affecting the c-mode frequency.

43. The method for determining φ angle error of the AT angle-of-cut test resonator, as recited in claim 33, wherein said test fluid is a gas.

44. The method for determining φ angle error of the AT angle-of-cut test resonator, as recited in claim 43, further comprising the step of testing a group of test resonators in a test chamber for a given frequency at one time.

45. The method for determining φ angle error of the AT angle-of-cut test resonator, as recited in claim 44, wherein said gas is nitrogen.

46. The method for determining φ angle error of the AT angle-of-cut test resonator, as recited in claim 45, wherein said test resonator is a near AT angle-of-cut test resonator.

47. A method for determining error in a φ angle of a BT angle-of-cut test resonator, comprising the steps of:

selecting a plurality of reference resonators having small φ angles-of-cut;

measuring a reference frequency of a b-mode in each of said plurality of reference resonators excited in ambient air;

measuring a reference frequency of the b-mode in each of said plurality of reference resonators excited in a test fluid;

calculating a plurality of normalized b-mode frequency changes between said reference air frequency and said reference fluid frequency;

measuring a frequency of the b-mode in the test resonator excited in said ambient air, said test resonator having an unknown φ angle-of-cut;

measuring a frequency of the b-mode in the test resonator excited in said test fluid at said b-mode frequency;

calculating a normalized test b-mode frequency change between said test air frequency and said test fluid frequency to determine a b-mode displacement ratio for said test resonator; and determining a deviation amount from said unknown φ angle-of-cut and 0°.

48. The method for determining φ angle error of the BT angle-of-cut test resonator, as recited in claim 47, wherein said small φ angles-of-cut are less than or equal to 7°.

49. The method for determining φ angle error of the BT angle-of-cut test resonator, as recited in claim 48, wherein said test fluid is water.

50. The method for determining φ angle error of the BT angle-of-cut test resonator, as recited in claim 49, wherein said test fluid is ambient pure water.

51. The method for determining φ angle error of the BT angle-of-cut test resonator, as recited in claim 50, further comprising the step of selecting said plurality of reference resonators with a surface roughness similar to said test resonator.

52. The method for determining φ angle error of the BT angle-of-cut test resonator, as recited in claim 51, further comprising the step of selecting said plurality of reference resonators with a surface contour similar to said test resonator.

53. The method for determining φ angle error of the BT angle-of-cut test resonator, as recited in claim 52, further comprising measuring an θ angle-of-cut in a first group of reference resonators before said selecting step.

54. The method for determining φ angle error of the BT angle-of-cut test resonator, as recited in claim 53, further comprising the step of comparing a reference air frequency measurement with a test air frequency measurement during said calculating step.

55. The method for determining φ angle error of the BT angle-of-cut test resonator, as recited in claim 54, further comprising the step of comparing a reference water frequency measurement with a test water frequency measurement during said calculating step.

56. The method for determining φ angle error of the BT angle-of-cut test resonator, as recited in claim 55, further comprising measuring said θ angle-of-cut and said φ angle-of-cut with an x-ray diffraction means.

57. The method for determining φ angle error of the BT angle-of-cut test resonator, as recited in claim 56, further comprising the steps of:

exciting an unplated blank of said test resonator by lateral field excitation from beneath said unplated blank;

UV-ozone cleaning said unplated blank to result in a low contact angle created by the UV-ozone;

applying a uniformly sized drop of water to an upper surface of said unplated blank; and said UV-ozone cleaning step causes said drop of water to spread from edge to edge of the unplated blank resulting in a thin, uniform layer of water affecting the b-mode frequency.

58. The method for determining φ angle error of the BT angle-of-cut test resonator, as recited in claim 48, wherein said test fluid is a gas.

59. The method for determining φ angle error of the BT angle-of-cut test resonator, as recited in claim 58, further comprising the step of testing a group of test resonators in a test chamber for a given frequency at one time.

60. The method for determining φ angle error of the BT angle-of-cut test resonator, as recited in claim 59, wherein said gas is nitrogen.

61. The method for determining φ angle error of the AT angle-of-cut test resonator, as recited in claim 60, wherein said test resonator is a near BT angle-of-cut test resonator.

62. A method for determining error in a φ angle of a rotated-y-cut ZTC angle-of-cut test resonator, comprising the steps of:

selecting a plurality of reference resonators having small φ angles-of-cut;

measuring a reference frequency of a quasi-shear mode in each of said plurality of reference resonators excited in ambient air;

measuring a reference frequency of the quasi-shear mode in each of said plurality of reference resonators excited in a test fluid;

calculating a plurality of normalized quasi-shear mode frequency changes between said reference air frequency and said reference fluid frequency;

measuring a test frequency of the quasi-shear mode in the test resonator excited in said ambient air, said test resonator having an unknown φ angle-of-cut;

measuring a test frequency of the quasi-shear mode in the test resonator excited in said test fluid at said quasi-shear mode frequency;

calculating a normalized test quasi-shear mode frequency change between said test air frequency and said test fluid frequency to determine a quasi-shear mode displacement ratio for said test resonator; and determining a deviation amount from said unknown φ angle-of-cut and 0°.

63. The method for determining φ angle error of the rotated-y-cut ZTC angle-of-cut test resonator, as recited in claim 62, wherein said small φ angles-of-cut are less than or equal to 7°.

64. The method for determining φ angle error of the rotated-y-cut ZTC angle-of-cut test resonator, as recited in claim 63, wherein said test fluid is water.

65. The method for determining φ angle error of the rotated-y-cut ZTC angle-of-cut test resonator, as recited in claim 64, wherein said test fluid is ambient pure water.

66. The method for determining φ angle error of the rotated-y-cut ZTC angle-of-cut test resonator, as recited in claim 65, further comprising the step of selecting said plurality of reference resonators with a surface roughness similar to said test resonator.

67. The method for determining φ angle error of the rotated-y-cut ZTC angle-of-cut test resonator, as recited in claim 66, further comprising the step of selecting said plurality of reference resonators with a surface contour similar to said test resonator.

68. The method for determining φ angle error of the rotated-y-cut ZTC angle-of-cut test resonator, as recited in claim 67, further comprising measuring an θ angle-of-cut in a first group of reference resonators before said selecting step.

69. The method for determining φ angle error of the rotated-y-cut ZTC angle-of-cut test resonator, as recited in claim 68, further comprising the step of comparing a reference air frequency measurement with a test air frequency measurement during said calculating step.

70. The method for determining φ angle error of the rotated-y-cut ZTC angle-of-cut test resonator, as recited in claim 69, further comprising the step of comparing a reference water frequency measurement with a water frequency measurement during said calculating step.

71. The method for determining φ angle error of the rotated-y-cut ZTC angle-of-cut test resonator, as recited in claim 70, further comprising measuring said θ angle-of-cut and said φ angle-of-cut with an x-ray diffraction means.

72. The method for determining φ angle error of the rotated-y-cut ZTC angle-of-cut test resonator, as recited in claim 71, further comprising the steps of:
    exciting an unplated blank of said test resonator by lateral field excitation from beneath said unplated blank;
    UV-ozone cleaning said unplated blank to result in a low contact angle created by the UV-ozone;
    applying a uniformly sized drop of water to an upper surface of said unplated blank; and
    said UV-ozone cleaning step causes said drop of water to spread from edge to edge of the unplated blank resulting in a thin, uniform layer of water affecting the quasi-shear mode frequency.

73. The method for determining φ angle error of the rotated-y-cut ZTC angle-of-cut test resonator, as recited in claim 63, wherein said test fluid is a gas.

74. The method for determining φ angle error of the rotated-y-cut ZTC angle-of-cut test resonator, as recited in claim 73, further comprising the step of testing a group of test resonators in a test chamber for a given frequency at one time.

75. The method for determining φ angle error of the rotated-y-cut ZTC angle-of-cut test resonator, as recited in claim 74, wherein said gas is nitrogen.

76. The method for determining φ angle error of the rotated-y-cut ZTC angle-of-cut test resonator, as recited in claim 75, wherein said test resonator is a near rotated-y-cut ZTC angle-of-cut test resonator.

77. A method for determining error in a φ angle of a test resonator, comprising the steps of:
    selecting a plurality of reference resonators having small φ angles-of-cut;
    measuring a reference frequency of a quasi-pure mode in each of said plurality of reference resonators excited in ambient air;
    measuring a reference frequency of the quasi-pure mode in each of said plurality of reference resonators excited in a test gas;
    calculating a plurality of normalized quasi-pure mode frequency changes between said reference air frequency and said reference gas frequency;
    measuring a frequency of the quasi-pure mode in the test resonator excited in said ambient air, said test resonator having an unknown φ angle-of-cut;
    measuring a frequency of the quasi-pure mode of the test resonator excited in said test gas at said quasi-pure mode frequency;
    calculating a normalized test quasi-pure mode frequency change between said test air frequency and said test gas frequency to determine a quasi-pure mode displacement ratio for said test resonator; and
    determining a deviation amount from said unknown φ angle-of-cut and 0°.

78. The method for determining φ angle error of the test resonator, as recited in claim 77, wherein said small φ angles-of-cut are less than or equal to 7°.

79. The method for determining φ angle error of the test resonator, as recited in claim 78, further comprising the step of selecting said test gas.

80. The method for determining φ angle error of the test resonator, as recited in claim 79, further comprising the step of selecting said plurality of reference resonators with a surface roughness similar to said test resonator.

81. The method for determining φ angle error of the test resonator, as recited in claim 80, further comprising the step of selecting said plurality of reference resonators with a surface contour similar to said test resonator.

82. The method for determining φ angle error of the test resonator, as recited in claim 81, further comprising the step of measuring an θ angle-of-cut in a first group of reference resonators before said resonator selecting step.

83. The method for determining φ angle error of the test resonator, as recited in claim 82, further comprising the step of comparing a reference air frequency measurement with a test air frequency measurement during said calculating step.

84. The method for determining φ angle error of the test resonator, as recited in claim 83, further comprising the step of comparing said a reference water frequency measurement with a water frequency measurement during said calculating step.

85. The method for determining φ angle error of the test resonator, as recited in claim 84, further comprising said test resonator having an AT angle-of-cut.

86. The method for determining φ angle error of the test resonator, as recited in claim 85, further comprising said quasi-pure mode frequency being a c-mode frequency.

87. The method for determining φ angle error of the test resonator, as recited in claim 84, further comprising said test resonator having a BT angle-of-cut.

88. The method for determining φ angle error of the test resonator, as recited in claim 87, further comprising said quasi-pure mode frequency being a b-mode frequency.

89. The method for determining φ angle error of the test resonator, as recited in claim 84, further comprising said test resonator having a rotated-y-cut ZTC angle-of-cut.

90. The method for determining φ angle error of the test resonator, as recited in claim 89, further comprising said quasi-pure mode frequency being a quasi-shear mode frequency.

91. The method for determining φ angle error of the test resonator, as recited in claim 84, further comprising each of said first group of reference resonators having said θ angle-of-cut.

92. The method for determining $\phi$ angle error of the test resonator, as recited in claim 91, further comprising measuring said $\theta$ angle-of-cut and said $\phi$ angle-of-cut with an x-ray diffraction means.

93. The method for determining $\phi$ angle error of the test resonator, as recited in claim 92, further comprising the step of exciting said plurality of reference resonators in said ambient air at a plurality of different frequencies during the measuring reference air frequency step.

94. The method for determining $\phi$ angle error of the test resonator, as recited in claim 93, further comprising the step of exciting said quasi-pure mode frequency during the measuring reference air frequency step.

95. The method for determining $\phi$ angle error of the test resonator, as recited in claim 94, further comprising the step of exciting said plurality of reference resonators in said test gas at a plurality of different frequencies during said measuring reference gas frequency step.

96. The method for determining $\phi$ angle error of the test resonator, as recited in claim 95, further comprising the step of exciting said quasi-pure mode frequency during the measuring reference gas frequency step.

97. The method for determining $\phi$ angle error of the test resonator, as recited in claim 96, further comprising the steps of:
 exciting an unplated blank of said test resonator by lateral field excitation from beneath said unplated blank; and
 applying a uniformly sized drop of water to an upper surface of said unplated blank.

98. The method for determining $\phi$ angle error of the test resonator, as recited in claim 97, further comprising the step of UV-ozone cleaning said unplated blank before the water applying step to result in a low contact angle created by the UV-ozone.

99. The method for determining $\phi$ angle error of the test resonator, as recited in claim 98, wherein said UV-ozone cleaning step causes said drop of water to spread from edge to edge of the unplated blank resulting in a thin, uniform layer of water affecting the quasi-pure mode frequency.

100. The method for determining $\phi$ angle error of the test resonator, as recited in claim 99, further comprising the step of measuring said test gas at a plurality of pressure values.

101. The method for determining $\phi$ angle error of the test resonator, as recited in claim 100, further comprising the step of testing a group of test resonators in a test chamber for a given frequency at one time.

102. The method for determining $\phi$ angle error of the test resonator, as recited in claim 101, further comprising the steps of:
 increasing a test chamber pressure value during the group testing step; and
 testing a multiple set of frequency measurements for said group all at once.

103. The method for determining $\phi$ angle error of the test resonator, as recited in claim 102, further comprising the step of repeating said frequency measurement steps.

104. The method for determining $\phi$ angle error of the test resonator, as recited in claim 103, further comprising the steps of:
 obtaining a plurality of reference gas pressure readings from said reference set of test resonators having known $\phi$ values; and
 comparing a plurality of frequency readings for each of said group of test resonators as a function of gas pressure with said plurality of gas reference pressure readings.

105. The method for determining $\phi$ angle error of the test resonator, as recited in claim 104, wherein said test gas is nitrogen.

* * * * *